US009422365B2

(12) United States Patent
Ohlsen et al.

(10) Patent No.: US 9,422,365 B2
(45) Date of Patent: Aug. 23, 2016

(54) PEPTIDE OR ARRANGEMENT OF PEPTIDES FORMING A *STAPHYLOCOCCUS AUREUS* EPITOPE BINDING SITE

(71) Applicant: JULIUS-MAXIMILIANS-UNIVERSITÄT WÜRZBURG, Würzburg (DE)

(72) Inventors: Knut Ohlsen, Würzburg (DE); Udo Lorenz, Güntersleben (DE); Roland E. Kontermann, Stuttgart (DE)

(73) Assignee: JULIUS-MAXIMILIANS-UNIVERSITÄT WÜRZBURG, Würzburg (DE)

( * ) Notice: Subject to any disclaimer, the term of this patent is extended or adjusted under 35 U.S.C. 154(b) by 0 days.

(21) Appl. No.: 14/346,435

(22) PCT Filed: Sep. 21, 2012

(86) PCT No.: PCT/EP2012/068703
§ 371 (c)(1),
(2) Date: Mar. 21, 2014

(87) PCT Pub. No.: WO2013/041707
PCT Pub. Date: Mar. 28, 2013

(65) Prior Publication Data

US 2014/0234339 A1 Aug. 21, 2014

Related U.S. Application Data

(60) Provisional application No. 61/545,763, filed on Oct. 11, 2011.

(30) Foreign Application Priority Data

Sep. 23, 2011 (EP) .................................... 11182598

(51) Int. Cl.

| | |
|---|---|
| *A61K 39/395* | (2006.01) |
| *A61K 39/40* | (2006.01) |
| *A61K 39/00* | (2006.01) |
| *A61K 45/00* | (2006.01) |
| *A61K 47/00* | (2006.01) |
| *C12N 5/07* | (2010.01) |
| *C12N 5/16* | (2006.01) |
| *C12P 21/08* | (2006.01) |
| *C07K 16/00* | (2006.01) |
| *C07K 16/12* | (2006.01) |
| *G01N 33/569* | (2006.01) |
| *A61K 38/00* | (2006.01) |

(52) U.S. Cl.
CPC ...... *C07K 16/1271* (2013.01); *G01N 33/56938* (2013.01); *A61K 38/00* (2013.01); *A61K 39/00* (2013.01); *A61K 2039/505* (2013.01); *C07K 16/1214* (2013.01); *C07K 2317/77* (2013.01); *C07K 2317/92* (2013.01); *C07K 2319/00* (2013.01)

(58) Field of Classification Search
CPC . A61K 38/00; A61K 2039/505; A61K 39/00; C07K 16/1271; C07K 2319/00; C07K 16/1214
See application file for complete search history.

(56) References Cited

FOREIGN PATENT DOCUMENTS

| | | | |
|---|---|---|---|
| WO | WO 02/072600 | A2 | 9/2002 |
| WO | WO 2010/133600 | A1 | 11/2010 |

OTHER PUBLICATIONS

Paul, William E., Fundamental Immunology, 3rd Edition, Raven Press, New York, Chap. 8, pp. 292-295 (1993).*
Rudikoff et al. (Proc. Natl. Acad. Sci. USA, 79(6):1979-1983.*
Colman P. M. (Research in Immunology, 145:33-36, 1994).*
Bendig M. M. (Methods: A Companion to Methods in Enzymology, 1995; 8:83-93).*
International Search Report, dated Dec. 6, 2012, issued in PCT/EP2012/068703.
Joseph M. Patti, "A humanized monoclonal antibody targeting *Staphylococcus aureus*", Vaccine 22S, Dec. 6, 2004, vol. 22, Suppl. 1, pp. S39-S43, XP-002687631, ISSN: 0264-410X.
K. Ohlsen et al., "Development of antibody-based therapy targeting immunodominant antigens of *Staphylococcus aureus*", International Journal of Medical Microbiology, vol. 297, No. Suppl. 1, Sep. 1, 2007, XP008124403, ISSN: 1438-4221, p. 128.
Knut Ohlsen et al., "Immunotherapeutic strategies to combat staphylococcal infections", International Journal of Medical Microbiology, IJMM Aug. 2010, vol. 300, No. 6, pp. 402-410, XP-002687632, ISSN: 1618-0607.
Udo Lorenz et al., "Functional Antibodies Targeting IsaA of *Staphylococcus aureus* Augment Host Immune Response and Open New Perspectives for Antibacterial Therapy", Antimicrobial Agents and Chemotherapy, Chemotherapy, vol. 55, No. 1, Jan. 2011, XP-002687630, ISSN: 0066-4804, pp. 165-173.

* cited by examiner

*Primary Examiner* — Gary Nickol
*Assistant Examiner* — Lakia Tongue
(74) *Attorney, Agent, or Firm* — Birch, Stewart, Kolasch & Birch, LLP

(57) ABSTRACT

The invention concerns a peptide or arrangement of peptides forming a *Staphylococcus aureus* epitope binding site comprising a first amino acid sequence and a second amino acid sequence, wherein the first amino acid sequence is at least 88% identical to sequence SEQ ID NO:1 and wherein the second amino acid sequence is at least 88% identical to sequence SEQ ID NO: 2.

20 Claims, 5 Drawing Sheets

SEQUENCE LISTING

```
<160> NUMBER OF SEQ ID NOS: 14

<210> SEQ ID NO 1
<211> LENGTH: 118
<212> TYPE: PRT
<213> ORGANISM: Artificial
<220> FEATURE:
<223> OTHER INFORMATION: Modified sequence of a sequence from mus
      musculus

<400> SEQUENCE: 1
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ser Asp Ile Asn Gly Asn Gly Ser Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Arg Gly Gly Tyr Tyr Ala Leu Asp Tyr Trp Gly Gln Gly Thr
            100                 105                 110

Thr Val Thr Val Ser Ser
            115

<210> SEQ ID NO 2
<211> LENGTH: 113
<212> TYPE: PRT
<213> ORGANISM: Artificial
<220> FEATURE:
<223> OTHER INFORMATION: Modified sequence of a sequence from mus
      musculus

<400> SEQUENCE: 2

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ile
            20                  25                  30

Asn Gly Asn Thr Tyr Leu His Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Leu Glu Leu Lys
            100                 105                 110

Arg

<210> SEQ ID NO 3
<211> LENGTH: 113
<212> TYPE: PRT
<213> ORGANISM: Artificial
<220> FEATURE:
<223> OTHER INFORMATION: Modified sequence of a sequence from mus
      musculus

<400> SEQUENCE: 3

Glu Ile Val Leu Thr Gln Ser Pro Gly Thr Leu Ser Leu Ser Pro Gly
1               5                   10                  15

Glu Arg Ala Thr Leu Ser Cys Arg Ser Ser Gln Ser Leu Val His Ile
            20                  25                  30

Asn Gly Asn Thr Tyr Leu His Trp Tyr Gln Gln Lys Pro Gly Gln Ala
        35                  40                  45

Pro Arg Leu Leu Ile Tyr Arg Val Ser Asn Arg Phe Ser Gly Ile Pro

```
                    50                  55                  60
Asp Arg Phe Ser Gly Ser Gly Ser Gly Thr Asp Phe Thr Leu Thr Ile
 65                  70                  75                  80

Ser Arg Leu Glu Pro Glu Asp Phe Ala Val Tyr Tyr Cys Ser Gln Ser
                 85                  90                  95

Thr His Val Pro Trp Thr Phe Gly Gly Gly Thr Lys Leu Glu Leu Lys
                100                 105                 110

Arg

<210> SEQ ID NO 4
<211> LENGTH: 448
<212> TYPE: PRT
<213> ORGANISM: Artificial
<220> FEATURE:
<223> OTHER INFORMATION: Sequence containing SEQ ID N0:1 and IgG1 heavy
      chain, human gamma1 allotype Gm1,17

<400> SEQUENCE: 4

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
                 20                  25                  30

Tyr Met Ser Trp Val Arg Gln Ala Pro Gly Lys Gly Leu Glu Trp Val
             35                  40                  45

Ser Asp Ile Asn Gly Asn Gly Ser Thr Tyr Tyr Pro Asp Thr Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Arg Arg Gly Gly Tyr Tyr Ala Leu Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
```

```
                290             295             300
Ser Val Leu Thr Val Leu His Gln Asp Trp Leu Asn Gly Lys Glu Tyr
305             310             315             320

Lys Cys Lys Val Ser Asn Lys Ala Leu Pro Ala Pro Ile Glu Lys Thr
                325             330             335

Ile Ser Lys Ala Lys Gly Gln Pro Arg Glu Pro Gln Val Tyr Thr Leu
                340             345             350

Pro Pro Ser Arg Asp Glu Leu Thr Lys Asn Gln Val Ser Leu Thr Cys
                355             360             365

Leu Val Lys Gly Phe Tyr Pro Ser Asp Ile Ala Val Glu Trp Glu Ser
                370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
                405             410             415

Arg Trp Gln Gln Gly Asn Val Phe Ser Cys Ser Val Met His Glu Ala
                420             425             430

Leu His Asn His Tyr Thr Gln Lys Ser Leu Ser Leu Ser Pro Gly Lys
                435             440             445

<210> SEQ ID NO 5
<211> LENGTH: 468
<212> TYPE: PRT
<213> ORGANISM: Artificial
<220> FEATURE:
<223> OTHER INFORMATION: SEQ ID NO:4 with leader sequence SEQ ID NO:8

<400> SEQUENCE: 5

Met Glu Thr Asp Thr Leu Leu Leu Trp Val Leu Leu Leu Trp Val Pro
1               5               10              15

Gly Ser Thr Gly Glu Val Gln Leu Leu Glu Ser Gly Gly Gly Leu Val
                20              25              30

Gln Pro Gly Gly Ser Leu Arg Leu Ser Cys Ala Ala Ser Gly Phe Thr
                35              40              45

Phe Ser Asn Tyr Tyr Met Ser Trp Val Arg Gln Ala Pro Gly Lys Gly
                50              55              60

Leu Glu Trp Val Ser Asp Ile Asn Gly Asn Gly Ser Thr Tyr Tyr
65              70              75              80

Pro Asp Thr Val Lys Gly Arg Phe Thr Ile Ser Arg Asp Asn Ser Lys
                85              90              95

Asn Thr Leu Tyr Leu Gln Met Asn Ser Leu Arg Ala Glu Asp Thr Ala
                100             105             110

Val Tyr Tyr Cys Val Arg Arg Gly Gly Tyr Tyr Ala Leu Asp Tyr Trp
                115             120             125

Gly Gln Gly Thr Thr Val Thr Val Ser Ser Ala Ser Thr Lys Gly Pro
                130             135             140

Ser Val Phe Pro Leu Ala Pro Ser Ser Lys Ser Thr Ser Gly Gly Thr
145             150             155             160

Ala Ala Leu Gly Cys Leu Val Lys Asp Tyr Phe Pro Glu Pro Val Thr
                165             170             175

Val Ser Trp Asn Ser Gly Ala Leu Thr Ser Gly Val His Thr Phe Pro
                180             185             190

Ala Val Leu Gln Ser Ser Gly Leu Tyr Ser Leu Ser Ser Val Val Thr
                195             200             205

Val Pro Ser Ser Ser Leu Gly Thr Gln Thr Tyr Ile Cys Asn Val Asn
```

```
            210                 215                 220
His Lys Pro Ser Asn Thr Lys Val Asp Lys Val Glu Pro Lys Ser
225                 230                 235                 240

Cys Asp Lys Thr His Thr Cys Pro Pro Cys Pro Ala Pro Glu Leu Leu
                    245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
        290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                    325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                    405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
        450                 455                 460

Ser Pro Gly Lys
465

<210> SEQ ID NO 6
<211> LENGTH: 219
<212> TYPE: PRT
<213> ORGANISM: Artificial
<220> FEATURE:
<223> OTHER INFORMATION: SEQ ID NO:2 with human IgG light chain K

<400> SEQUENCE: 6

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ile
            20                  25                  30

Asn Gly Asn Thr Tyr Leu His Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Leu Glu Leu Lys
```

```
                100                 105                 110
Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 7
<211> LENGTH: 239
<212> TYPE: PRT
<213> ORGANISM: Artificial
<220> FEATURE:
<223> OTHER INFORMATION: SEQ ID NO:6 with leader sequence SEQ ID NO:8

<400> SEQUENCE: 7

Met Glu Thr Asp Thr Leu Leu Leu Trp Val Leu Leu Leu Trp Val Pro
1               5                   10                  15

Gly Ser Thr Gly Asp Val Val Met Thr Gln Thr Pro Leu Ser Leu Ser
            20                  25                  30

Val Thr Pro Gly Gln Pro Ala Ser Ile Ser Cys Arg Ser Ser Gln Ser
        35                  40                  45

Leu Val His Ile Asn Gly Asn Thr Tyr Leu His Trp Tyr Leu Gln Lys
    50                  55                  60

Pro Gly Gln Ser Pro Gln Leu Leu Ile Tyr Arg Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Trp Thr Phe Gly Gly Gly Thr Lys
        115                 120                 125

Leu Glu Leu Lys Arg Thr Val Ala Ala Pro Ser Val Phe Ile Phe Pro
        130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
        210                 215                 220

Gly Leu Ser Ser Pro Val Thr Lys Ser Phe Asn Arg Gly Glu Cys
225                 230                 235
```

-continued

```
<210> SEQ ID NO 8
<211> LENGTH: 20
<212> TYPE: PRT
<213> ORGANISM: Mus musculus

<400> SEQUENCE: 8

Met Glu Thr Asp Thr Leu Leu Leu Trp Val Leu Leu Leu Trp Val Pro
1               5                   10                  15

Gly Ser Thr Gly
            20

<210> SEQ ID NO 9
<211> LENGTH: 444
<212> TYPE: PRT
<213> ORGANISM: Artificial
<220> FEATURE:
<223> OTHER INFORMATION: SEQ ID NO:1 with IgG2 heavy chain, allotype G2m
      (23)

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ser Asp Ile Asn Gly Asn Gly Gly Ser Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Arg Gly Gly Tyr Tyr Ala Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
```

```
                290                 295                 300
Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
                355                 360                 365

Phe Tyr Pro Ser Asp Ile Ser Val Glu Trp Glu Ser Asn Gly Gln Pro
                370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
                435                 440

<210> SEQ ID NO 10
<211> LENGTH: 464
<212> TYPE: PRT
<213> ORGANISM: Artificial
<220> FEATURE:
<223> OTHER INFORMATION: SEQ ID NO:9 with leader sequence SEQ ID NO:8

<400> SEQUENCE: 10

Met Glu Thr Asp Thr Leu Leu Leu Trp Val Leu Leu Leu Trp Val Pro
1               5                   10                  15

Gly Ser Thr Gly Glu Val Gln Leu Leu Glu Ser Gly Gly Gly Leu Val
                20                  25                  30

Gln Pro Gly Gly Ser Leu Arg Leu Ser Cys Ala Ala Ser Gly Phe Thr
            35                  40                  45

Phe Ser Asn Tyr Tyr Met Ser Trp Val Arg Gln Ala Pro Gly Lys Gly
        50                  55                  60

Leu Glu Trp Val Ser Asp Ile Asn Gly Asn Gly Gly Ser Thr Tyr Tyr
65              70                  75                  80

Pro Asp Thr Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Val Arg Arg Gly Gly Tyr Tyr Ala Leu Asp Tyr Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
```

```
                    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
            245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
            275                 280                 285

Glu Val Gln Phe Asn Trp Tyr Val Asp Gly Val Glu Val His Asn Ala
290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
            355                 360                 365

Pro Pro Ser Arg Glu Glu Met Thr Lys Asn Gln Val Ser Leu Thr Cys
370                 375                 380

Leu Val Lys Gly Phe Tyr Pro Ser Asp Ile Ser Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro Gly Lys
450                 455                 460

<210> SEQ ID NO 11
<211> LENGTH: 445
<212> TYPE: PRT
<213> ORGANISM: Artificial
<220> FEATURE:
<223> OTHER INFORMATION: SEQ ID NO:1 with IgG4 heavy chain

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ser Asp Ile Asn Gly Asn Gly Gly Ser Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Arg Gly Gly Tyr Tyr Ala Leu Asp Tyr Trp Gly Gln Gly Thr
            100                 105                 110

Thr Val Thr Val Ser Ser Ala Ser Thr Lys Gly Pro Ser Val Phe Pro
```

```
            115                 120                 125
Leu Ala Pro Cys Ser Arg Ser Thr Ser Glu Ser Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Lys Thr Tyr Thr Cys Asn Val Asp His Lys Pro Ser
        195                 200                 205
Asn Thr Lys Val Asp Lys Arg Val Glu Ser Lys Tyr Gly Pro Pro Cys
    210                 215                 220
Pro Ser Cys Pro Ala Pro Glu Phe Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser Gln Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Gln Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly Lys
        435                 440                 445

<210> SEQ ID NO 12
<211> LENGTH: 465
<212> TYPE: PRT
<213> ORGANISM: Artificial
<220> FEATURE:
<223> OTHER INFORMATION: SEQ ID NO:11 with leader sequence SEQ ID NO:8

<400> SEQUENCE: 12

Met Glu Thr Asp Thr Leu Leu Leu Trp Val Leu Leu Leu Trp Val Pro
1               5                   10                  15
Gly Ser Thr Gly Glu Val Gln Leu Leu Glu Ser Gly Gly Gly Leu Val
            20                  25                  30
Gln Pro Gly Gly Ser Leu Arg Leu Ser Cys Ala Ala Ser Gly Phe Thr
        35                  40                  45
```

```
Phe Ser Asn Tyr Tyr Met Ser Trp Val Arg Gln Ala Pro Gly Lys Gly
 50                  55                  60

Leu Glu Trp Val Ser Asp Ile Asn Gly Asn Gly Gly Ser Thr Tyr Tyr
 65                  70                  75                  80

Pro Asp Thr Val Lys Gly Arg Phe Thr Ile Ser Arg Asp Asn Ser Lys
                     85                  90                  95

Asn Thr Leu Tyr Leu Gln Met Asn Ser Leu Arg Ala Glu Asp Thr Ala
                100                 105                 110

Val Tyr Tyr Cys Val Arg Arg Gly Gly Tyr Tyr Ala Leu Asp Tyr Trp
                115                 120                 125

Gly Gln Gly Thr Thr Val Thr Val Ser Ser Ala Ser Thr Lys Gly Pro
130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
                195                 200                 205

Val Pro Ser Ser Ser Leu Gly Thr Lys Thr Tyr Thr Cys Asn Val Asp
210                 215                 220

His Lys Pro Ser Asn Thr Lys Val Asp Lys Arg Val Glu Ser Lys Tyr
225                 230                 235                 240

Gly Pro Pro Cys Pro Ser Cys Pro Ala Pro Glu Phe Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser Gln Glu Asp
                275                 280                 285

Pro Glu Val Gln Phe Asn Trp Tyr Val Asp Gly Val Glu Val His Asn
290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
                340                 345                 350

Thr Ile Ser Lys Ala Lys Gly Gln Pro Arg Glu Pro Gln Val Tyr Thr
                355                 360                 365

Leu Pro Pro Ser Gln Glu Glu Met Thr Lys Asn Gln Val Ser Leu Thr
                370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
                420                 425                 430

Ser Arg Trp Gln Glu Gly Asn Val Phe Ser Cys Ser Val Met His Glu
                435                 440                 445

Ala Leu His Asn His Tyr Thr Gln Lys Ser Leu Ser Leu Ser Leu Gly
450                 455                 460
```

```
<210> SEQ ID NO 13
<211> LENGTH: 120
<212> TYPE: PRT
<213> ORGANISM: Mus musculus

<400> SEQUENCE: 13

Met Ala Asp Val Lys Leu Val Glu Ser Gly Gly Gly Leu Val Lys Leu
1               5                   10                  15

Gly Gly Ser Leu Lys Leu Ser Cys Ser Ala Ser Gly Phe Thr Phe Ser
            20                  25                  30

Asn Tyr Tyr Met Ser Trp Val Arg Gln Thr Pro Glu Lys Arg Leu Glu
        35                  40                  45

Leu Val Ala Asp Ile Asn Gly Asn Gly Gly Ser Thr Tyr Tyr Pro Asp
    50                  55                  60

Thr Val Lys Gly Arg Phe Thr Ile Ser Arg Asp Asn Ala Lys Asn Thr
65                  70                  75                  80

Leu Tyr Leu Gln Met Ser Ser Leu Lys Ser Glu Asp Thr Ala Leu Tyr
                85                  90                  95

Tyr Cys Val Arg Arg Gly Gly Tyr Tyr Ala Leu Asp Tyr Trp Gly Gln
            100                 105                 110

Gly Thr Thr Val Thr Val Ser Ser
        115                 120

<210> SEQ ID NO 14
<211> LENGTH: 113
<212> TYPE: PRT
<213> ORGANISM: Mus musculus

<400> SEQUENCE: 14

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ile
            20                  25                  30

Asn Gly Asn Thr Tyr Leu His Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Leu Lys
            100                 105                 110

Arg
```

PEPTIDE OR ARRANGEMENT OF PEPTIDES FORMING A *STAPHYLOCOCCUS AUREUS* EPITOPE BINDING SITE

CROSS REFERENCE TO RELATED APPLICATIONS

This application is the National Phase of PCT/EP2012/068703 filed on Sep. 21, 2012, which claims priority under 35 U.S.C. §119(e) to U.S. Provisional Application No. 61/545,763 filed on Oct. 11, 2011, under 35 U.S.C §119(a) to patent application Ser. No. 11/182,598.0 filed in Europe on Sep. 23, 2011, all of which are hereby expressly incorporated by reference into the present application.

The invention concerns a peptide or arrangement of peptides forming a *Staphylococcus aureus* (=*S. aureus*) epitope binding site, a kit containing this peptide or arrangement of peptides, a use of this peptide or arrangement of peptides, a cell line which produces antibodies comprising this peptide or arrangement of peptides and a method of treatment.

From WO 2010/133600 A1 antibodies or fragments thereof directed against an *S. aureus* epitope of IsaA are known. These antibodies have a binding site formed by a heavy chain with a first variable region and a light chain with a second variable region wherein the sequence of the first variable region may be SEQ ID NO:13 and the sequence of the second variable region may be SEQ ID NO:14. The effectiveness of antibodies vis-à-vis *S. aureus* in a mammal depends on killing of *S. aureus* by phagocytosis by phagocytizing blood cells. The antibodies known from WO 2010/133600 A1 accelerated the phagocytosis process. After 30 minutes of incubation the killing of *S. aureus* by human neutrophils in the presence of the antibodies specific for an epitope of IsaA has been enhanced by about 25% to 30% compared to an unspecific control antibody.

The object of the present invention is to provide a *S. aureus* epitope binding site that is very effective in an antibody or fragment of antibody with respect to the killing of *S. aureus* by phagocytizing blood cells and therefore is well suited for a treatment of infections caused by *Staphylococcus aureus*. Furthermore, the binding site should be well suited for a detection of *S. aureus*. A further object of the present invention is to provide a kit containing the binding site, a use of the binding site, a cell line secreting antibodies, antibody fragments, ScFvs or ScFvFcs comprising the binding site and a method of treatment.

According to the invention a peptide or arrangement of peptides forming a *Staphylococcus aureus* epitope binding site comprising a first amino acid sequence and a second amino acid sequence is provided. The first amino acid sequence is at least 88% identical to sequence SEQ ID NO:1 and the second amino acid sequence is at least 88% identical to SEQ ID NO:2.

In an embodiment the first amino acid sequence is at least 90% identical, in particular at least 92.5% identical, in particular at least 95% identical, in particular at least 97.5% identical, in particular 100% identical, to sequence SEQ ID NO:1. The second amino acid sequence is at least 90% identical, in particular at least 92.5% identical, in particular at least 95% identical, in particular at least 97.5% identical, in particular 100% identical, to sequence SEQ ID NO:2.

The first amino acid sequence may be part of the heavy chain and/or the second amino acid sequence may be part of the light chain of an antibody or antibody fragment. In this case the first amino acid sequence and the second amino acid sequence form the variable region of the antibody or antibody fragment. The binding site can also be formed by a single chain variable fragment. In this case the first amino acid sequence and the second amino acid sequence are comprised by a single chain variable fragment (scFv) or by a single chain variable fragment comprising an Fc fragment of an antibody (scFvFc). The Fc fragment enhances phagocytosis of *S. aureus* to which the scFvFc has bound.

The inventors modified the binding region of one of the antibodies known from WO 2010/133600 A1 and thereby developed a binding site that is more effective in support of killing of *S. aureus* by phagocytosis by phagocytizing blood cells in heparinized human whole blood than the known antibody. As can be seen from the following alignment sequence SEQ ID NO:1 differs in 17 form 118 amino acids from the corresponding sequence SEQ ID NO:13 and SEQ ID NO:2 differs in 8 from 113 amino acids from SEQ ID NO:14 known from WO 2010/133600 A1:

```
SEQ ID NO: 1      EVQLLESGGGLVQPGGSLRLSCAASGFTFSNYYMSWVRQAPGKGLEWVSDINGNGGSTYY    60
                   V L ESGGGLV  GGSL LSC ASGFTFSNYYMSWVRQ P K LE V DINGNGGSTYY
SEQ ID NO: 13   MADVKLVESGGGLVKLGGSLKLSCSASGFTFSNYYMSWVRQTPEKRLELVADINGNGGSTYY    62

SEQ ID NO: 1    PDTVKGRFTISRDNSKNTLYLQMNSLRAEDTAVYYCVRRGGYYALDYWGQGTTVTVSS       118
                PDTVKGRFTISRDN KNTLYLQM SL  EDTA YYCVRRGGYYALDYWGQGTTVTVSS
SEQ ID NO: 13   PDTVKGRFTISRDNAKNTLYLQMSSLKSEDTALYYCVRRGGYYALDYWGQGTTVTVSS       120

SEQ ID NO: 2    DVVMTQTPLSLSVTPGQPASISCRSSQSLVHINGNTYLHWYLQKPGQSPQLLIYRVSNRF     60
                DVVMTQTPLSL V  G  ASISCRSSQSLVHINGNTYLHWYLQKPGQSP LLIYRVSNRF
SEQ ID NO: 14   DVVMTQTPLSLPVSLGDQASISCRSSQSLVHINGNTYLHWYLQKPGQSPKLLIYRVSNRF     60

SEQ ID NO: 2    SGVPDRFSGSGSGTDFTLKISRVEAEDVGVYYCSQSTHVPWTFGGGTKLELKR            113
                SGVPDRFSGSGSGTDFTLKISRVEAED GVY CSQSTHVPWTFGGGTKLELKR
SEQ ID NO: 14   SGVPDRFSGSGSGTDFTLKISRVEAEDLGVYFCSQSTHVPWTFGGGTKLELKR            113
```

Identical amino acids are displayed in the interspace between the sequences.

Antibodies containing the variable region comprising the first amino acid sequence and the second amino acid sequence exhibit high affinity to the immunodominant structure IsaA in methicillin resistant and methicillin sensitive *S. aureus* and a high specificity with respect to the binding to this structure.

The antibody may be a monoclonal antibody, in particular an antibody of the IgG type, in particular of the IgG1 type, the IgG2 type, or the IgG4 type. The fragment may be an Fab fragment, Fab/c fragment, Fv fragment, Fab' fragment or $F(ab')_2$ fragment. These fragments are particularly useful for the detection of *S. aureus* because the cell wall of *S. aureus* contains protein A which unspecifically binds immunglobulins via their Fc-parts.

In an embodiment of the invention the antibody is a recombinant antibody produced in cells of a cell line, in particular an insect cell line or a mammalian cell line, in particular a Chinese hamster ovary (CHO) cell line or a hybridoma cell line. The part of the antibody which is not formed by the first amino acid sequence and the second amino acid sequence is at least 85% identical, in particular at least 90% identical, in particular at least 92.5% identical, in particular at least 95% identical, in particular at least 97.5% identical, in particular 100% identical, to the corresponding part of a human antibody. The light chain of the antibody can comprise sequence SEQ ID NO:6, in particular sequence SEQ ID NO:7 and the heavy chain can comprise the sequence SEQ ID NO:4, in particular SEQ ID NO:5, sequence SEQ ID NO:9, in particular sequence SEQ ID NO:10, or sequence SEQ ID NO:11, in particular SEQ ID NO:12. Sequences SEQ ID NO:7, SEQ ID NO:5, SEQ ID NO:10 and SEQ ID NO:12 comprise the leader sequence SEQ ID NO:8 which is from the MOPC 63, Ig kappa chain V-III of KV3A9_mouse. This leader sequence enables a good expression in mammalian cells. The sequence SEQ ID NO:4 comprises sequence SEQ ID NO:1 and an IgG1 heavy chain, human γ1 allotype Gm 1,17. Sequence SEQ ID NO:6 comprises sequence SEQ ID NO:2 and the IgG light chain K. Sequence SEQ ID NO:9 comprises sequence SEQ ID NO:1 and the IgG2 heavy chain, allotype G2m(23). Sequence SEQ ID NO:11 comprises SEQ ID NO:1 and an IgG4 heavy chain.

The peptide or arrangement of peptides according to the invention may be used as a medicament. Especially they may be used as a medicament for the treatment of a human being or an animal which human being or animal has an infection with S. aureus, especially methicillin resistant or methicillin sensitive S. aureus, or is at risk of getting such an infection. The treatment in the sense of this invention comprises prophylaxis. The animal may be a mammal. The human being or the animal may have a mastitis, an S. aureus bacteremia, in particular a primary or secondary bacteremia, a blood stream infection, in particular a primary or secondary blood stream infection, a prosthetic infection, a graft infection, a soft tissue infection, a surgery associated infection, an infant or newborn infection, a dialysis associated infection, a pneumonia, a bone infection, or a sepsis caused by the infection. The mastitis may be a bovine mastitis. If a cow has bovine mastitis no useable milk is produced by the cow and if the cow is treated with antibiotics as it is usual in this case the milk produced by this cow has to be discarded until no antibiotics are contained in the milk of this cow. This disadvantage of the usual treatment may be avoided by use of the peptide or arrangement of peptides according to the invention as a medicament for the treatment of the bovine mastitis.

The peptide or arrangement of peptides may be present in mixture with at least one other peptide or arrangement of peptides directed against at least one further epitope of S. aureus. This further epitope may be located on the antigen on which the epitope is located, i. e. IsaA, or on a further antigen. The use of such a mixture as a medicament may be more efficient than the use of a medicament which solely contains the peptide or arrangement of peptides according to the invention. This may be owing to the high variability of S. aureus that causes different extents of expression of the antigens on different strains such that more bacteria are recognized by the mixture of antibodies or fragments than by the antibodies or fragments alone.

The peptide or arrangement of peptides can be present in a mixture with at least one antibiotic. In the human being or animal to be treated with the medicament mutated S. aureus may be present in addition to common S. aureus. The mutated S. aureus may have mutated IsaA that cannot be recognized by the peptide or arrangement of peptides according to the invention. In this case the antibiotic may be effective against the mutated S. aureus.

The peptide or arrangement of peptides according to the invention may be present in a mixture with plasma or blood of a mammal, especially a human being. The inventors found that the peptide or arrangement of peptides according to the invention mixed with plasma may be much more effective than the peptide or arrangement of peptides according to the invention contained in a saline solution.

The medicament may be a medicament that is prepared for systemic and/or local application. The inventors have recognized that the treatment of a severe S. aureus infection with the peptide or arrangement of peptides according to the invention results in a significant reduction of the mortality rates and number of S. aureus in the organs of the treated human being or animal.

The invention also concerns a kit containing the peptide or arrangement of peptides according to the invention for the detection, especially a highly specific detection, of S. aureus.

The invention further concerns the use of the peptide or arrangement of peptides according to the invention for a detection, especially a highly specific detection, of S. aureus.

Furthermore, the invention concerns a cell line, in particular an insect cell line or a mammalian cell line, in particular a Chinese hamster ovary (CHO) cell line or a hybridoma cell line, which produces an antibody, antibody fragment, ScFv or ScFvFc as specified above.

The invention further concerns a method of treatment of a human being or an animal which human being or animal has an infection with Staphylococcus aureus, especially methicillin resistant or methicillin sensitive Staphylococcus aureus, or is at risk of getting such an infection, wherein the peptide or arrangement of peptides according to the invention is administered to the human being or the animal. The peptide or arrangement of peptides is administered in a dosage that is sufficient to reduce the amount of S. aureus or to cause an elimination of S. aureus in the human being or the animal. The peptide or arrangement of peptides may be mixed with a suitable carrier.

The human being or the animal may have mastitis, an S. aureus bacteremia, in particular a primary or secondary bacteremia, a blood stream infection, in particular a primary or secondary blood stream infection, a prosthetic infection, a graft infection, a soft tissue infection, a surgery associated infection, an infant or newborn infection, a dialysis associated infection, a pneumonia, a bone infection, or a sepsis caused by the infection.

The peptide or arrangement of peptides may be present in a mixture with at least one other peptide or arrangement of peptides directed against at least one further epitope of S. aureus. The peptide or arrangement of peptides may be mixed with plasma or blood of a mammal, especially of a human being, before it is administered. The peptide or arrangement of peptides may be administered topically or systemically, in particular intravenously, intrapulmonary, intraperitoneally, nasally or sublingually. They may also be administered together with at least one antibiotic.

EMBODIMENTS OF THE INVENTION

ScFv molecules containing sequences SEQ ID NOs:1 and 2, SEQ ID NOs:1 and 3 as well as other sequences have been expressed in E. coli and tested for binding and affinity in ELISA and competitive ELISA. The results showed that affinity of an ScFv molecule containing sequences SEQ ID NO:1 and SEQ ID NO:2 is about 10 times higher than affinity of an ScFv molecule containing sequences SEQ ID NO:1 and SEQ ID NO:3.

Vector constructs for the expression of complete antibodies has been transfected in CHO cells. IgG1 heavy chain, human γ1 allotype Gm1,17 according to sequence SEQ ID NO:4 (comprising sequence SEQ ID NO:1) with the Igk leader sequence SEQ ID NO:8 (resulting in sequence SEQ ID NO:5) and IgG light chain K according to SEQ ID NO:6 (comprising sequence SEQ ID NO:2) with the Igk leader sequence SEQ ID NO:8 (resulting in sequence SEQ ID NO:7) have been expressed to form antibody UK66-2. To investigate the influence of the isotype on functional activity IgG2 and IgG4 isotypes have been synthesized.

For this the IgG1 heavy chain has been replaced by IgG2 heavy chain, allotype G2m (23) according to sequence SEQ ID NO:9 with the Igk leader sequence SEQ ID NO:8 (resulting in sequence SEQ ID NO:10) or IgG4 heavy chain according to sequence SEQ ID NO:11 with the Igk leader sequence SEQ ID NO:8 (resulting in sequence SEQ ID NO:12).

After expression IgG1 antibodies have been purified from the supernatant of the CHO cells via a protein A column. The purified antibodies have been tested for the kinetics of binding, binding in ELISA, competitive ELISA, Western Blot and immunofluorescence und for function in phagocytosis assays with human phagocytizing blood cells. In funktional assays the antibody comprising sequences SEQ ID NOs:1 and 2 (UK66-2) enhanced oxidative burst und killing of S. aureus significantly more than known antibody UK66.

The kinetics of binding of IsaA to immobilized antibody UK66-2 was determined by means of label-free surface plasmon resonance using the BIACORE®2000 system (GE Healthcare Europe GmbH, Munzinger Strasse 5, 79111 Freiburg, Germany). Reversible immobilization of the antibody UK66-2 was performed using an anti Fab antibody. Interaction analyses were performed using HBS-EP buffer (10 mM HEPES pH 7.4, 150 mM NaCl, 3.4 mM EDTA, 0.005% Tween 20 (polyoxyethylene (20) sorbitan monolaurate)). Sensorgrams were recorded at a flow rate of 30 µl/min at 25° C.

Affinities and rate constants for association ($k_{on}$) and for dissociation ($k_{off}$) were calculated using the BIA evaluation software 4.0.1 (Biacore) fitting the obtained sensorgrams to a 1:1 Langmuir binding model. In this way a dissociation constant $K_D$ of 4.8 nM was determined in two independent measurements. Rate constants for association and dissociation of the interaction between UK66-2 and IsaA were determined to be $3.7 \times 10^5$ $M^{-1}s^{-1}$ ($k_{on}$) and $1.8 \times 10^{-3}$ $s^{-1}$ ($k_{off}$), respectively.

Figure 1:
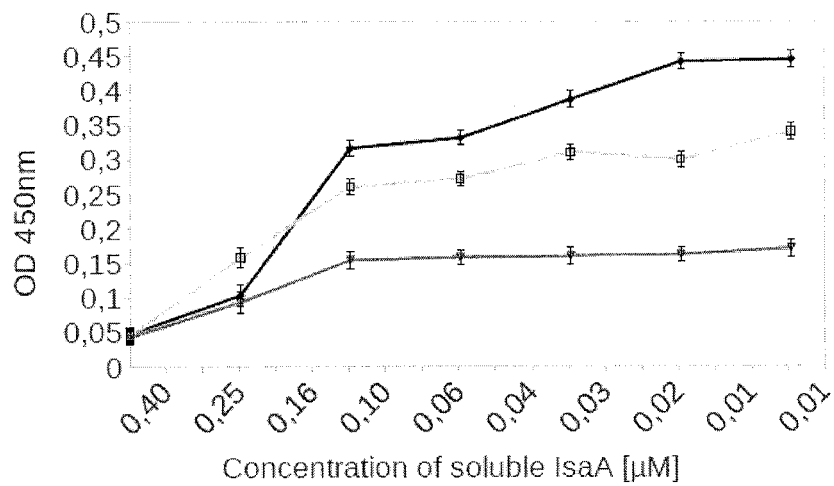
FIG. 1 shows the result of a competitive ELISA to determine binding of different anti-IsaA antibodies to the IsaA antigen.

FIG. 1 shows the result of a competitive ELISA to determine binding of different anti-IsaA antibodies to soluble recombinant IsaA antigen. The optical density at 450 nm indicates binding of the antibodies to IsaA. Soluble IsaA was added in different concentrations. The three lines represent the results received with the following anti IsaA antibodies:

Upper line at 0.01 µM soluble IsaA: UK66 (reference antibody known from WO 2010/133600 A1)

Middle line at 0.01 µM soluble IsaA: UK66-2 (antibody with a binding site comprising sequences SEQ ID NO:1 and SEQ ID NO:2)

Lower line at 0.01 µM soluble IsaA: UK66-3 (antibody with a binding site comprising sequences SEQ ID NO:1 and SEQ ID NO:3)

Method Description:

Nunc-Maxisorp 96-well plates were coated with 50 µl/well of IsaA (0.5 µg/well in 1×PBS) and incubated at 4° C. overnight. The next day the plates were washed three times with PBS pH 7.4 containing 0.05% Tween 20 (polyoxyethylene (20) sorbitan monolaurate) (PBST). After washing blocking was performed by addition of 200 µl 5% skimmed milk powder/PBS and incubated for 1 h at room temperature. The wells were washed twice with PBST (0.05%) and primary anti-IsaA antibody was added in serial concentrations ranging from 0.4 µM to 0.01 µM. The primary anti-IsaA-IgG1 antibodies were diluted in 2.5% skimmed milk powder/PBS and incubated for 1 h at 37° C. The wells were then washed three times with PBST (0.05%) and 50 µl of horseradish peroxidase linked secondary antibody 1:5000 diluted in 2.5% skimmed milk powder/PBS was added and incubated for 1 h at 37° C. The wells were washed with PBST (0.05%) four times and 50 µl of TMB (3,3',5,5'-tetramethylbenzadine) (Thermo Scientific Pierce ELISA substrate) was added and incubated for 15 min at 37° C. The reaction was stopped with 100 µl of 1N $H_2SO_4$ and optical density of the substrate reaction was analyzed with an ELISA plate reader at OD 450 nm.

Figure 2:
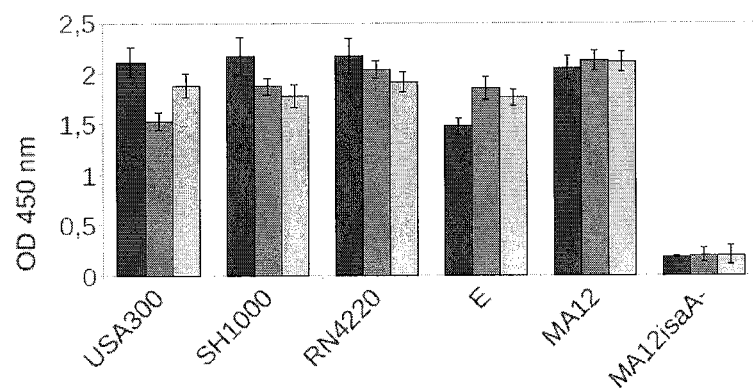
FIG. 2 shows a bacterial cell ELISA to determine binding of different anti-IsaA antibodies to different S. aureus strains.

FIG. 2 shows a bacterial cell ELISA to determine binding of different anti-IsaA antibodies to the S. aureus strains USA300, SH1000, RN4220, E, MA12 and MA12isaA-. In MA12isaA- the immunodominant structure IsaA has been deleted. The optical density at 450 nm indicates binding of the antibodies to bacterial cells. The three columns represent the results received with the following anti IsaA antibodies:

Left column: antibody UK66 (reference antibody)

Middle column: antibody UK66-2

Right column: antibody UK66-3.

Method Description:

The strains of S. aureus were cultured in B media at 37° C. overnight. The bacteria were pelleted by centrifugation at 13000 rpm for 1 minute and washed with PBS (phosphate buffered saline). After the centrifugation step the pellet was resuspended in 1 ml PBS. A bacteria suspension containing $5 \times 10^7$ bacteria/50 µl was prepared. Nunc-Maxisorp 96-well plates were coated with 50 µl/well of the bacteria suspension and incubated at 4° C. overnight. The next day the plates were washed three times with PBS pH 7.4 containing 0.05% Tween 20 (polyoxyethylene (20) sorbitan monolaurate) (PBST). After washing blocking was performed by addition of 200 µl 5% skimmed milk powder/PBS and incubated for 1 h at room temperature. The wells were washed twice with PBST (0.05%) and primary anti-IsaA antibody was added. The primary anti-IsaA-IgG1 antibodies were diluted 1:2000 in 2.5% skimmed milk powder/PBS and 50 µl/well were added and incubated for 1 h at 37° C. The wells were then washed three times with PBST (0.05%) and 50 µl of horseradish peroxidase linked secondary antibody 1:5000 diluted in 2.5% skimmed milk powder/PBS was added and incubated for 1 h at 37° C. The wells were washed with PBST (0.05%) four times and 50 µl of TMB (3,3',5,5'-tetramethylbenzadine) (Thermo Scientific Pierce ELISA substrate) was added and incubated for 15 min at 37° C. The reaction was stopped with 100 µl of 1N $H_2SO_4$ and optical density of the substrate reaction was analyzed with an ELISA plate reader at OD 450 nm.

Figure 3:
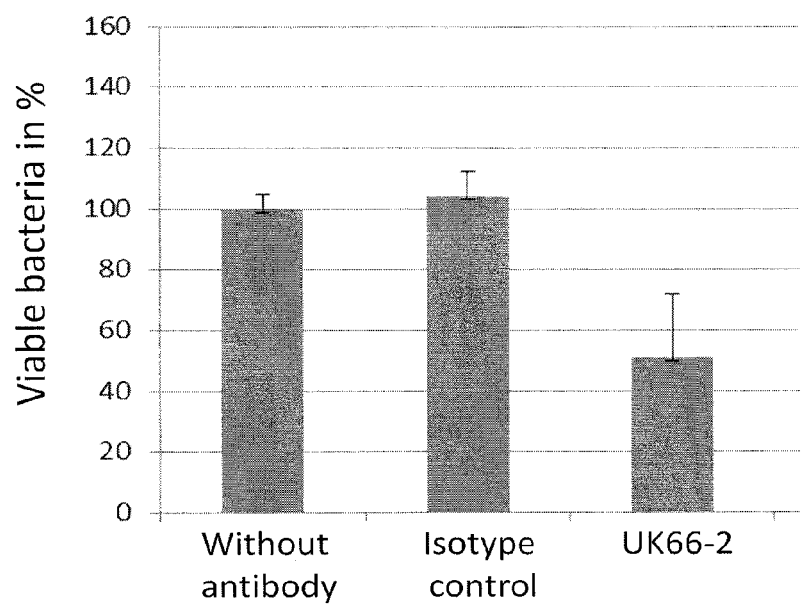
FIG. 3 shows the quantification of killing of S. aureus strain Newman by phagocytosis by phagocytizing blood cells in heparinized human whole blood.

FIG. 3 shows the quantification of killing of *S. aureus* strain Newman by phagocytosis by phagocytizing blood cells in heparinized human whole blood. Bacteria were incubated 30 min with the heparinized human whole blood. The number of viable bacteria after incubation without antibody solution was set 100% (left column). Killing was significantly increased in the presence of UK66-2 (right column) compared to isotype control antibodies (middle column).

Method Description:

*S. aureus* strain Newman was cultured in LB medium at 37° C. overnight. The bacteria were pelleted by centrifugation at 13000 rpm for 1 minute and washed with PBS. The centrifugation step was repeated and the bacteria were resuspended in 1 ml PBS. Bacteria solution of $5 \times 10^7$ bacteria/20 µl was prepared. 100 µl of heparinized blood was added into 1.5 ml tubes and stored on ice. 20 µl of bacterial suspension and antibody solution were added, excluded the negative control sample which contained bacteria but no antibodies. The samples were incubated at 37° C. for 30 min with constant movement overhead in a hybridisation oven. Phagocytosis was stopped by placing the samples on ice. Blood cells were lysed with 0.1% fresh prepared Saponin (20 min on ice). Two serial dilutions of the samples were prepared. 20 µl of $10^{-2}$, $10^{-3}$ and $10^{-4}$ dilution, respectively were plated in duplicate on LB plates and incubated at 37° C. for 24 h. The colonies were counted and killing was calculated setting the number of viable bacteria in blood without antibody solution as 100%.

Figure 4:
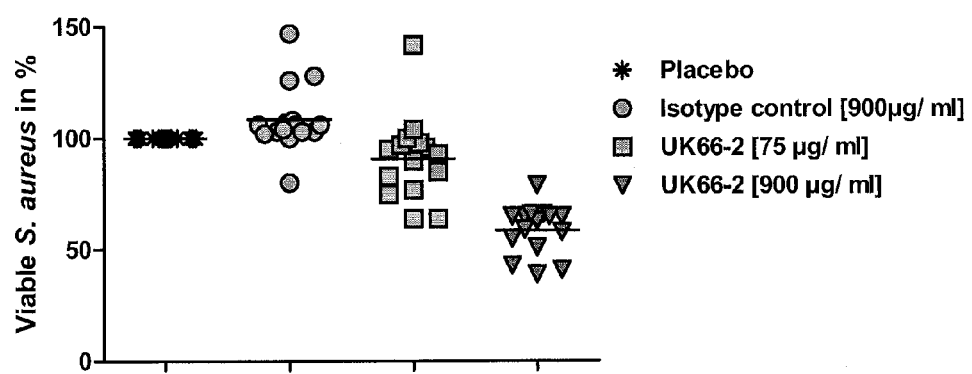
FIG. 4 shows the quantification of killing of S. aureus strain Newman by phagocytosis by phagocytizing blood cells in heparinized human whole blood from healthy blood donators (n=15).
Figure 5:
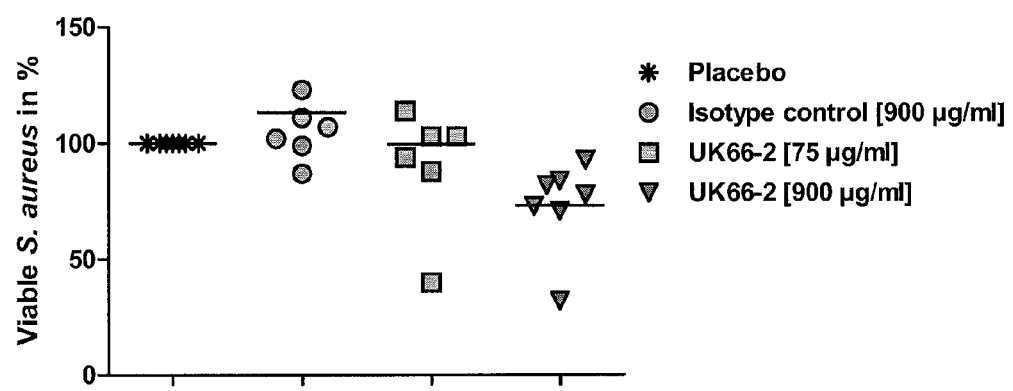
FIG. 5 shows the quantification of killing of S. aureus strain Newman by phagocytosis by phagocytizing blood cells in heparinized human whole blood from dialysis patients.

FIG. 4 shows the quantification of killing of *S. aureus* strain Newman by phagocytosis by phagocytizing blood cells in heparinized human whole blood from healthy blood donators (n=15). FIG. 5 shows the quantification of killing of *S. aureus* strain Newman by phagocytosis by phagocytizing blood cells in heparinized human whole blood from dialysis patients (n=7). In both cases bacteria were incubated 60 min with the heparinized blood. The number of viable bacteria after incubation without antibody solution was set 100% (left scatter plot "Placebo"). Killing was significantly increased in the presence of UK66-2 (third and fourth scatter plot "UK66-2 [75 µg/ml]" and "UK66-2[900 µg/ml]") compared to isotype control antibodies (second scatter plot "Isotype control [900 µg/ml]").

Method Description:

*S. aureus* strain Newman was cultured in LB medium at 37° C. overnight. The bacteria were pelleted by centrifugation at 13000 rpm for 1 minute and washed with PBS. The centrifugation step was repeated and the bacteria were resuspended in 1 ml PBS. Bacteria solution of $5 \times 10^7$ bacteria/20 µl was prepared. 100 µl of heparinized blood was added into 1.5 ml tubes and stored on ice. 20 µl of bacterial suspension and antibody solution were added, excluded the negative control sample which contained bacteria but no antibodies. The samples were incubated at 37° C. for 60 min with constant movement overhead in a hybridisation oven. Phagocytosis was stopped by placing the samples on ice. Blood cells were lysed with 0.1% fresh prepared Saponin (20 min on ice). Two serial dilutions of the samples were prepared. 20 µl of $10^{-2}$, $10^{-3}$ and $10^{-4}$ dilution, respectively were plated in duplicate on LB plates and incubated at 37° C. for 24 h. The colonies were counted and killing was calculated. The number of viable bacteria in blood without antibody solution was set 100%.

Figure 6:
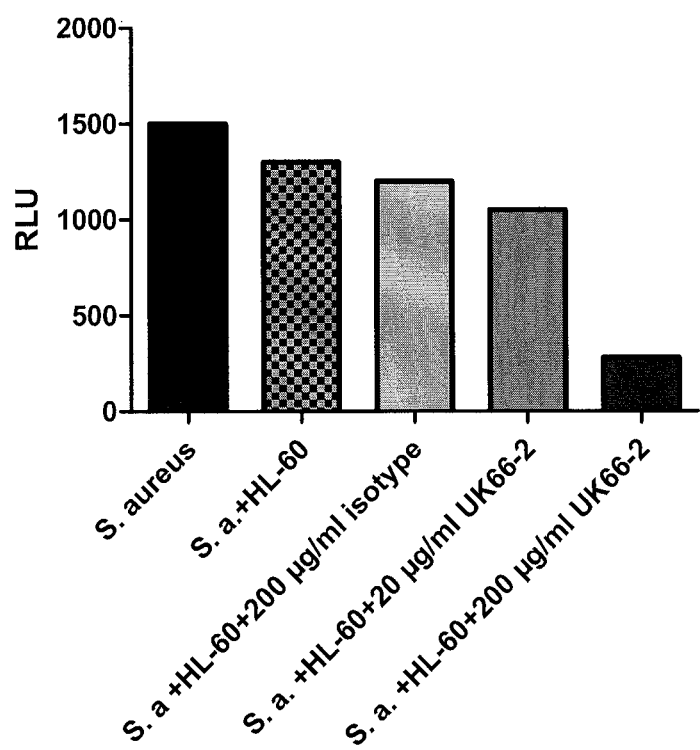
FIG. 6 shows the opsonophagocytic killing of bioluminescent S. aureus strain Newman (Newlux) in the presence of two concentrations of anti-IsaA antibody UK66-2 versus isotype control in HL-60 cells.

FIG. 6 shows killing of bioluminescent *S. aureus* (S. a.) strain Newman (Newlux) in the presence of two concentrations of anti-IsaA antibody UK66-2 (20 µg/ml and 200 µg/ml versus isotype control (200 µg/ml) in HL-60 cells. Determination of relative number of surviving bacteria was performed by measurement of bioluminescence. Surviving bacteria are given as light emission (RLU=relative light units). Bacterial killing is concentration dependent with UK66-2 and is not observed with an isotype-matched human IgG1 control antibody.

Method Description:

A single colony of *S. aureus* strain Newman harbouring the luxABCED operon was used to inoculate 5 ml LB medium. Since the luxABCED operon causes a luminescence in living but not in dead bacteria the luminescence correlates with the number of living bacteria. The bacteria were cultivated overnight and 50 µl of this culture were used to inoculate 5 ml LB medium supplemented with 30 µg/ml kanamycin. The culture was cultivated on a rotary shaker at 200 rpm for 4-6 h at 37° C. Bioluminescence of the bacteria was determined using a Lumat LB 9501 luminometer (Berthold Technologies, Bad Wildbad, Germany). The culture was ready for performing the assay when 100 µl of the culture generated bioluminescence signals ranged between 16000-24000 relative light units (RLU). Following cultivation, the bacteria were washed twice in phosphate buffered saline (PBS) and resuspended in Opti-MEM® medium (Life Technologies, Darmstadt, Germany) to a final concentration of 1×10/ml. Phagocytic HL-60 cells were differentiated with 0.8% DMF for 5 days and resuspended to $1 \times 10^8$ cells/ml in Opti-MEM®, and 50 µl per well were seeded in a 96-well tissue culture plate (Greiner Bio-One, Frickenhausen, Germany). Antibody solution (50 µl) was added followed by 100 µl of *S. aureus* ($1 \times 10^9$/ml). HL-60 cells, antibody and bacteria were incubated at 37° C. and bioluminescence was measured continuously at 15 min intervals for 240 min to determine the optimal signal-noise ratio. All assays were performed in triplicate and repeated at least three times. Bioluminescence was determined using the multi-mode reader Infinite 200 Pro (TECAN, Mannedorf, Switzerland).

The invention claimed is:

1. An antibody or antigen binding fragment, comprising:
a variable heavy chain sequence comprising SEQ ID NO: 1; and
a variable light chain sequence comprising SEQ ID NO: 2;
wherein said antibody or antigen binding fragment specifically binds to an epitope of *Staphylococcus aureus*.

2. The antibody or antigen binding fragment of claim 1, wherein the antibody or antigen binding fragment enables killing of *Staphylococcus aureus* by promoting phagocytosis by blood cells in a subject.

3. The antibody or antigen binding fragment of claim 1, wherein the heavy chain and/or the light chain are comprised by a single chain variable fragment (scFv) or by a single chain variable fragment comprising an Fc fragment of an antibody (scFvFc).

4. The antibody or antigen binding fragment of claim 1, wherein the antibody or antigen binding fragment is a monoclonal antibody.

5. The antibody or antigen binding fragment of claim 1, wherein the fragment is an Fab fragment, Fab/c fragment, Fv fragment, Fab' fragment or F(ab')$_2$ fragment.

6. The antibody or antigen binding fragment of claim 1, wherein the antibody or antigen binding fragment is a recombinant antibody produced in cells of a cell line.

7. The antibody or antigen binding fragment of claim 1, wherein the light chain comprises sequence SEQ ID NO:6, and the heavy chain comprises sequence SEQ ID NO:4, sequence SEQ ID NO:9, or sequence SEQ ID NO:11.

8. The antibody or antigen binding fragment of claim 1 suitable for use as a medicament.

9. The antibody or antigen binding fragment of claim 8, wherein the medicament is a medicament for the treatment of a human being or an animal which human being or animal has an infection with *Staphylococcus aureus* or is at risk of getting such an infection.

10. The antibody or antigen binding fragment of claim 9, wherein the human being or the animal has a mastitis, an *S. aureus* bacteremia, a blood stream infection, a prosthetic infection, a graft infection, a soft tissue infection, a surgery associated infection, an infant or newborn infection, a dialysis associated infection, a pneumonia, a bone infection, or a sepsis caused by the infection.

11. The antibody or antigen binding fragment of claim 8, wherein the antibody or antigen binding fragment is present in a mixture with at least one other antibody or antigen binding fragment directed against at least one further epitope of *Staphylococcus aureus*.

12. The antibody or antigen binding fragment of claim 8, wherein the antibody or antigen binding fragment is present in a mixture with at least one antibiotic.

13. The antibody or antigen binding fragment of claim 8, wherein the antibody or antigen binding fragment is present in a mixture with plasma or blood of a mammal.

14. The antibody or antigen binding fragment of claim 8, wherein the medicament is a medicament for systemic and/or local application.

15. Kit containing the antibody or antigen binding fragment of claim 1 for the detection of *Staphylococcus aureus*.

16. Method of treatment of a human being or an animal which human being or animal has an infection with *Staphylococcus aureus* or is at risk of getting such an infection, wherein the antibody or antigen binding fragment as claimed in claim 1 is administered to the human being or the animal.

17. Method according to claim 16, wherein the human being or the animal has a mastitis, an *S. aureus* bacteremia, a blood stream infection, a prosthetic infection, a graft infection, a soft tissue infection, a surgery associated infection, an infant or newborn infection, a dialysis associated infection, a pneumonia, a bone infection, or a sepsis caused by the infection.

18. Method as claimed in claim 16, wherein the antibody or antigen binding fragment is mixed with plasma or blood of a mammal before it is administered.

19. Method as claimed in claim 16, wherein the antibody or antigen binding fragment is administered topically or systemically.

20. Method as claimed in claim 16, wherein the antibody or antigen binding fragment is administered together with at least one antibiotic.

* * * * *